(12) United States Patent
Liu et al.

(10) Patent No.: US 9,920,349 B2
(45) Date of Patent: Mar. 20, 2018

(54) METHODS AND MATERIALS FOR ENZYMATIC SYNTHESIS OF MOGROSIDE COMPOUNDS

(71) Applicant: Evolva SA, Reinach (CH)

(72) Inventors: Yaoquan Liu, Palo Alto, CA (US); Jung Yeop Lee, Cupertino, CA (US); Monika Khare, Cupertino, CA (US)

(73) Assignee: Evolva SA, Reinach (CH)

( * ) Notice: Subject to any disclaimer, the term of this patent is extended or adjusted under 35 U.S.C. 154(b) by 0 days.

(21) Appl. No.: 14/356,782

(22) PCT Filed: Nov. 19, 2012

(86) PCT No.: PCT/IB2012/002857
§ 371 (c)(1),
(2) Date: May 7, 2014

(87) PCT Pub. No.: WO2013/076577
PCT Pub. Date: May 30, 2013

(65) Prior Publication Data
US 2014/0308698 A1 Oct. 16, 2014

Related U.S. Application Data

(60) Provisional application No. 61/563,303, filed on Nov. 23, 2011.

(51) Int. Cl.
*C12P 33/20* (2006.01)
*C12P 19/18* (2006.01)
*C12P 33/00* (2006.01)

(52) U.S. Cl.
CPC .............. *C12P 33/20* (2013.01); *C12P 19/18* (2013.01); *C12P 33/00* (2013.01)

(58) Field of Classification Search
CPC .......... C12P 19/18; C12P 33/00; C12P 333/20
See application file for complete search history.

(56) References Cited

U.S. PATENT DOCUMENTS 8,257,948 B1 * 9/2012 Markosyan ........... A23L 1/2366 426/548
2007/0118916 A1 5/2007 Puzio et al.
2015/0322473 A1 11/2015 Liu et al.

FOREIGN PATENT DOCUMENTS

| EP | 1510573 | 3/2005 | |
|---|---|---|---|
| EP | 1897951 | 12/2010 | |
| RU | 2008123244 | 12/2009 | |
| WO | WO 0112845 A1 * | 2/2001 | ........... C12N 9/1051 |
| WO | WO 2007/061753 | 5/2007 | |
| WO | WO2008062165 | 5/2008 | |
| WO | WO2008065370 | 6/2008 | |
| WO | WO2010106318 | 9/2010 | |
| WO | 2011/153378 | 12/2011 | |
| WO | 2014/086842 | 6/2014 | |

OTHER PUBLICATIONS

Poppenberger B. et al., Heterologous Expression of *Arabidopsis* UDP-Glucosyltransferases in *Saccharomyces cerevisiae* for Production of Zearalenone-4-O-Glucoside, Applied and Environmental Microbiology, Jun. 2006, vol. 72, No. 6, pp. 4404-4410.*
Shao H. et al., Crystal Structures of a Multifunctional Triterpene/Flavonoid Glycosyltransferase from Medicago truncatula, The Plant Cell, 2005, vol. 17, pp. 3141-3154.*
Nilsson B.L. et al., Chemical Synthesis of Proteins, Annu. Rev. Biophys. Biomol. Struct., 2005, vol. 34, pp. 91-118; Author manuscript, Available in PMC Mar. 25, 2010, total pp. 1-38.*
Brochado et al., "Improved vanillin production in baker's yeast through in silico design," Microb Cell Fact. 9:84 (2010).
Chiu et al., "Biotransformation of mogrosides from Siraitia grosvenorii Swingle by *Saccharomyces cerevisiae*," J Agric Food Chem. 61(29):7127-34 (2013).
Donald et al., "Effects of overproduction of the catalytic domain of 3-hydroxy-3-methylglutaryl coenzyme A reductase on squalene synthesis in *Saccharomyces cerevisiae*," Appl Environ Microbiol. 63(9):3341-4 (1997).
Hamberger & Bak, "Plant P450s as versatile drivers for evolution of species-specific chemical diversity," Philos Trans R Soc Lond B Biol Sci. 368(1612):20120426 (2013).
Kirby et al., "Engineering triterpene production in *Saccharomyces cerevisiae*-beta-amyrin synthase from Artemisia annua," FEBS J. 275(8):1852-9 (2008).
Seki, Licorice beta-amyrin 11-oxidase, a cytochrome P450 with a key role in the biosynthesis of the triterpene sweetener glycyrrhizin, Proc Natl Acad Sci U S A. 105(37):14204-9 (2008).
Shibuya et al., "Cucurbitadienol synthase, the first committed enzyme for cucurbitacin biosynthesis, is a distinct enzyme from cycloartenol synthase for phytosterol biosynthesis," Tetrahedron 60(33):6995-7003 (2004).
Thompson et al., "CLUSTAL W: improving the sensitivity of progressive multiple sequence alignment through sequence weighting, position-specific gap penalties and weight matrix choice," Nucleic Acids Res. 22(22):4673-80 (1994).
Ukiya et al., "Inhibitory effects of cucurbitane glycosides and other triterpenoids from the fruit of Momordica grosvenori on epstein-barr virus early antigen induced by tumor promoter 12-O-tetradecanoylphorbol-13-acetate," J Agric Food Chem. 50(23):6710-5 (2002).
International Search Report issued by the International Searching Authority for International Application No. PCT/IB2012/002857, dated May 14, 2013 (pp. 1-6).
Written Opinion of the International Searching Authority for International Application No. PCT/IB2012/002857, dated May 14, 2013 (pp. 1-7).
International Preliminary Report on Patentability issued by the International Preliminary Examining Authority for International Application No. PCT/IB2012/002857, dated Jan. 9, 2014 (pp. 1-13).
International Search Report issued by the International Searching Authority for International Application No. PCT/EP2013/075510, dated May 4, 2015 (pp. 1-7).
Written Opinion of the International Searching Authority for International Application No. PCT/EP20131075510, dated Apr. 23, 2014 (pp. 1-14).

(Continued)

*Primary Examiner* — Satyendra K Singh
(74) *Attorney, Agent, or Firm* — McDonnell Boehnen Hulbert & Berghoff LLP

(57) ABSTRACT

Methods and materials for enzymatic synthesis of mogroside compounds described.

16 Claims, 5 Drawing Sheets

(56) References Cited

OTHER PUBLICATIONS

Written Opinion of the International Preliminary Examining Authority for International Application No. PCT/EP2013/075510, dated Feb. 4, 2015 (pp. 1-14).
Written Opinion of the International Preliminary Examining Authority for International Application No. PCT/EP2013/075510, dated May 5, 2015 (pp. 1-15).
Takemoto, et al, Yakugaku Zasshi, 103:1151-1154; 1155-1166; 1167-1173 (1983).
Kasai, et al., Agric. Biol. Chem. 53:3347-3349 (1989).
Matsumoto, Chem. Pharm., Bull. 28:2030-2032 (1990).
Chaturvedula, et al., J. Carbohydrate Chem., 30:16-26 (2011).
Sonnhammer, et al., Nucl. Acids Res., 26:320-322 (1998).
Sonnhammer, et al., Proteins, 28:405-420 (1997).
Bateman, et al., Nucl. Acis Res., 27:260-262 (1999).
Tang, et al., BMC Genomics, 12:1-13 (2011).
Richman, et al., The Plant Journal, 41:56-67 (2005).
Bowles, et al., Current Opinion in Plant Biology, 8:254-263 (2005).
Li, et al., Chemical & Pharmaceutical Bulletin, 54:1425-1428 (2006).
Jia, et al., Natural Product Communications, 4:769-772 (2009).
Xiong Mian-jing et al., "Biosynthesis of triterpene glycoside in Lo Han Kuo," Guangdong Pharmaceutical University 27(5):544-5. English abstract provided, Oct. 2011.
UniProt Database Accession No. AT223684, "Stevia rebaudiana protein SEQ ID No. 10008," Feb. 3, 2011 (1 page).
English Translation of First Office Action issued by the State Intellectual Property Office of People's Republic of China for CN Application No. 201280057518.8, dated Oct. 23, 2015 (pp. 1-11).
Communication pursuant to Rules 161(1) and 162 EPC issued by the European Patent Office for European Application No. 12819015.4, dated Jul. 1, 2014 (pp. 1-2).
Response to Communication pursuant to Rules 161(1) and 162 EPC issued by the European Patent Office for European Application No. 12819015.4, dated Dec. 19, 2014 (pp. 1-6).
Communication pursuant to Article 94(3) EPC issued by the European Patent Office for European Application No. 12819015.4, dated Mar. 18, 2015 (pp. 1-7).
Response to Communication pursuant to Article 94(3) EPC issued by the European Patent Office for European Application No. 12819015.4, dated Sep. 18, 2015 (pp. 1-8).
Decision to grant a European patent pursuant to Article 97(1) EPC issued by the European Patent Office for European Application No. 12819015.4, dated Mar. 17, 2016 (pp. 1-2).
Guo et al., "Protein tolerance to random amino acid change," Proc Natl Acad Sci U 22;101(25):9205-10 (2004).
Wikipedia: "Mogroside," Internet Archive Wayback Machine Jan. 9, 2014 (Jan. 1, 2014), retrieved from the Internet: URL:https://web.archive.org/web/20140109130110/http://en.wikipedia.org/wiki/Mogroside [retrieved on Apr. 14, 2016] (pp. 1-2).
Non-Final Office Action for U.S. Appl. No. 14/504,109, dated Jun. 29, 2016, pp. 1-13.
Final Office Action for U.S. Appl. No. 14/504,109, dated Sep. 8, 2016, pp. 1-18.
International Search Report and Written Opinion of the International Searching Authority for International Application No. PCT/EP2015/072645, dated May 20, 2016 (pp. 1-39).
Frankel et al., "Characterization of diphtheria fusion proteins targeted to the human interleukin-3 receptor", Protein Eng., v.13, No. 8, p. 575-581 abstract, p. 579-580 (2000).
Pakula et al., "Genetic analysis of protein stability and function," Anna. Rev. Genet., v.23, 289-310 (p. 305-306) (1989).
Poppenberger et al., "Detoxification of the Fusarium mycotoxin deoxynivalenol by a UDP-glucosyltransferase from *Arabidopsis thaliana*," J Biol Chem. 278(48):47905-14 (Epub 2003).
International Preliminary Report on Patentability issued by the International Preliminary Examining Authority for International Application No. PCT/EP2015/072645, dated Apr. 4, 2017 (pp. 1-28).
Non-Final Office Action for U.S. Appl. No. 14/442,694, dated May 16, 2017, pp. 1-13.

\* cited by examiner

FIGURE 3

UGT73C3 (SEQ ID NO: 01)

MATEKTHQFHPSLHFVLFPFMAQGHMIPMIDIARLLAQRGVTITIVTTPHNAARFKNVLNRAIESGLAINILHVKFPYQEFGLPEGKENIDS
LDSTELMVPFFKAVNLLEDPVMKLMEEMKPRPSCLISDWCLPYTSIIAKNFNIPKIVFHGMGCFNLLCMHVLRRNLEILENVKSDEEYFL
VPSFPDRVEFTKLQLPVKANASGDWKEIMDEMVKAEYTSYGVIVNTFQELEPPYVKDYKEAMDGKVWSIGPVSLCNKAGADKAERGS
KAAIDQDECLQWLDSKEEGSVLYVCLGSICNLPLSQLKELGLGLEESRRSFIWVIRGSEKYKELFEWMLESGFEERIKERGLLIKGWAP
QVLILSHPSVGGFLTHCGWNSTLEGITSGIPLITWPLFGDQFCNQKLVVQVLKAGVSAGVEEVMKWGEEDKIGVLVDKEGVKKAVEEL
MGDSDDAKERRRRVKELGELAHKAVEKGGSHSNITLLLQDIMQLAQFKN

UGT73C5 (SEQ ID NO: 02)

MVSETTKSSPLHFVLFPFMAQGHMIPMVDIARLLAQRGVIITIVTTPHNAARFKNVLNRAIESGLPINLVQVKFPYLEAGLQEGQENIDSL
DTMERMIPFFKAVNFLEEPVQKLIEEMNPRPSCLISDFCLPYTSKIAKNFNIPKILFHGMGCFCLLCMHVLRKNREILDNLKSDKELFTVP
DFPDRVEFTRTQVPVETYVPAGDWKDIFDGMVEANETSYGVIVNSFQELEPAYAKDYKEVRSGKAWTIGPVSLCNKVGADKAERGNK
SDIDQDECLKWLDSKKHGSVLYVCLGSICNLPLSQLKELGLGLEESQRPFIWVIRGWEKYKELVEWFSESGFEDRIQDRGLLIKGWSP
QMLILSHPSVGGFLTHCGWNSTLEGITAGLPLLTWPLFADQFCNEKLVVEVLKAGVRSGVEQPMKWGEEEKIGVLVDKEGVKKAVEEL
MGESDDAKERRRRAKELGDSAHKAVEEGGSSHSNISFLLQDIMELAEPNN

UGT73C6 (SEQ ID NO: 03)

MAFEKNNEPFPLHFVLFPFMAQGHMIPMVDIARLLAQRGVLITIVTTPHNAARFKNVLNRAIESGLPINLVQVKFPYQEAGLQEGQENM
DLLTTMEQITSFFKAVNLLKEPVQNLIEEMSPRPSCLISDMCLSYTSEIAKKFKIPKILFHGMGCFCLLCVNVLRKNR

FIGURE 3 – CONTINUED

EILDNLKSDKEYFIVPYFPDRVEFTRPQVPVETYVPAGWKEILEDMVEADKTSYGVIVNSFQELEPAYAKDFKEARSGKAWTIGPVSLC
NKVGVDKAERGNKSDIDQDECLEWLDSKEPGSVLYVCLGSICNLPLSQLLELGLGLEESQRPFIWVIRGWEKYKELVEWFSESGFEDR
IQDRGLLIKGWSPQMLILSHPSVGGFLTHCGWNSTLEGITAGLPMLTWPLFADQFCNEKLVVQILKVGVSAEVKEVMKWGEEEKIGVL
VDKEGVKKAVEELMGESDDAKERRRRAKELGESAHKAVEEGGSSHSNITFLLQDIMQLAQSNN

UGT73E1 (SEQ ID NO: 04)

MSPKMVAPPTNLHFVLFPLMAQGHLVPMVDIARILAQRGATVTIITTPYHANRVRPVISRAIATNLKIQLLELQLRSTEAGLPEGCESFDQ
LPSFEYWKNISTAIDLLQQPAEDLLRELSPPPDCIISDFLFPWTTDVARRLNIPRLVFNGPGCFYLLCIHVAITSNILGENEPVSSNTERVV
LPGLPDRIEVTKLQIVGSSRPANVDEMGSWLRAVEAEKASFGIVVNTFEELEPEYVEEYKTVKDKMMWCIGPVSLCNKTGPDLAERGN
KAAITEHNCLKWLDERKLGSVLYVCLGSLARISAAQAIELGLGLESINRPFIWCVRNETDELKTWFLDGFEERVRDRGLIVHGWAPQVLI
LSHPTIGGFLTHCGWNSTIESITAGVPMITWPFFADQFLNEAFIVEVLKIGVRIGVERACLFGEEDKVGVLVKKEDVKKAVECLMDEDED
GDQRRKRVIELAKMAKIAMAEGGSSYENVSSLIRDVTETVRAPH

UGT85C2 (SEQ ID NO: 05)

MDAMATTEKKPHVIFIPFPAQSHIKAMLKLAQLLHHKGLQITFVNTDFIHNQFLESSGPHCLDGAPGFRFETIPDGVSHSPEASIPIRESL
LRSIETNFLDRFIDLVTKLPDPPTCIISDGFLSVFTIDAAKKLGIPVMMYWTLAACGFMGFYHIHSLIEKGFAPLKDASYLTNGYLDTVIDW
VPGMEGIRLKDFPLDWSTDLNDKVLMFTTEAPQRSHKVSHHIFHTFDELEPSIIKTLSLRYNHIYTIGPLQLLLDQIPEEKKQTGITSLHGY
SLVKEEPECFQWLQSKEPNSVVYVNFGSTTVMSLEDMTEFGWGLANSNHYFLWIIRSNLVIGENAVLPPELEEHIKKRGFIASWCSQE
KVLKHPSVGGFLTHCGWGSTIESLSAGVPMICWPYSWDQLTNCRYICKEWEVGLEMGTKVKRDEVKRLVQELMGEGGHKMRNKAK
DWKEKARIAIAPNGSSSLNIDKMVKEITVLARN

SEQUENCE LISTING

<160> NUMBER OF SEQ ID NOS: 5

<210> SEQ ID NO 1
<211> LENGTH: 496

<212> TYPE: PRT
<213> ORGANISM: Arabidopsis thaliana

<400> SEQUENCE: 1

```
Met Ala Thr Glu Lys Thr His Gln Phe His Pro Ser Leu His Phe Val
1               5                   10                  15

Leu Phe Pro Phe Met Ala Gln Gly His Met Ile Pro Met Ile Asp Ile
            20                  25                  30

Ala Arg Leu Leu Ala Gln Arg Gly Val Thr Ile Thr Ile Val Thr Thr
        35                  40                  45

Pro His Asn Ala Ala Arg Phe Lys Asn Val Leu Asn Arg Ala Ile Glu
    50                  55                  60

Ser Gly Leu Ala Ile Asn Ile Leu His Val Lys Phe Pro Tyr Gln Glu
65                  70                  75                  80

Phe Gly Leu Pro Glu Gly Lys Glu Asn Ile Asp Ser Leu Asp Ser Thr
                85                  90                  95

Glu Leu Met Val Pro Phe Phe Lys Ala Val Asn Leu Leu Glu Asp Pro
            100                 105                 110

Val Met Lys Leu Met Glu Glu Met Lys Pro Arg Pro Ser Cys Leu Ile
        115                 120                 125

Ser Asp Trp Cys Leu Pro Tyr Thr Ser Ile Ile Ala Lys Asn Phe Asn
    130                 135                 140

Ile Pro Lys Ile Val Phe His Gly Met Gly Cys Phe Asn Leu Leu Cys
145                 150                 155                 160

Met His Val Leu Arg Arg Asn Leu Glu Ile Leu Glu Asn Val Lys Ser
                165                 170                 175

Asp Glu Glu Tyr Phe Leu Val Pro Ser Phe Pro Asp Arg Val Glu Phe
            180                 185                 190

Thr Lys Leu Gln Leu Pro Val Lys Ala Asn Ala Ser Gly Asp Trp Lys
        195                 200                 205

Glu Ile Met Asp Glu Met Val Lys Ala Glu Tyr Thr Ser Tyr Gly Val
    210                 215                 220

Ile Val Asn Thr Phe Gln Glu Leu Glu Pro Pro Tyr Val Lys Asp Tyr
225                 230                 235                 240

Lys Glu Ala Met Asp Gly Lys Val Trp Ser Ile Gly Pro Val Ser Leu
                245                 250                 255

Cys Asn Lys Ala Gly Ala Asp Lys Ala Glu Arg Gly Ser Lys Ala Ala
            260                 265                 270

Ile Asp Gln Asp Glu Cys Leu Gln Trp Leu Asp Ser Lys Glu Glu Gly
        275                 280                 285

Ser Val Leu Tyr Val Cys Leu Gly Ser Ile Cys Asn Leu Pro Leu Ser
    290                 295                 300

Gln Leu Lys Glu Leu Gly Leu Gly Leu Glu Ser Arg Arg Ser Phe
305                 310                 315                 320

Ile Trp Val Ile Arg Gly Ser Glu Lys Tyr Lys Glu Leu Phe Glu Trp
                325                 330                 335

Met Leu Glu Ser Gly Phe Glu Glu Arg Ile Lys Glu Arg Gly Leu Leu
            340                 345                 350

Ile Lys Gly Trp Ala Pro Gln Val Leu Ile Leu Ser His Pro Ser Val
        355                 360                 365

Gly Gly Phe Leu Thr His Cys Gly Trp Asn Ser Thr Leu Glu Gly Ile
    370                 375                 380

Thr Ser Gly Ile Pro Leu Ile Thr Trp Pro Leu Phe Gly Asp Gln Phe
385                 390                 395                 400
```

```
Cys Asn Gln Lys Leu Val Val Gln Val Leu Lys Ala Gly Val Ser Ala
                405                 410                 415

Gly Val Glu Glu Val Met Lys Trp Gly Glu Asp Lys Ile Gly Val
            420                 425                 430

Leu Val Asp Lys Glu Gly Val Lys Lys Ala Val Glu Glu Leu Met Gly
            435                 440                 445

Asp Ser Asp Ala Lys Glu Arg Arg Arg Val Lys Glu Leu Gly
450                 455                 460

Glu Leu Ala His Lys Ala Val Glu Lys Gly Gly Ser Ser His Ser Asn
465                 470                 475                 480

Ile Thr Leu Leu Gln Asp Ile Met Gln Leu Ala Gln Phe Lys Asn
                485                 490                 495

<210> SEQ ID NO 2
<211> LENGTH: 495
<212> TYPE: PRT
<213> ORGANISM: Arabidopsis thaliana

<400> SEQUENCE: 2

Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
                20                  25                  30

Leu Leu Ala Gln Arg Gly Val Ile Thr Ile Val Thr Thr Pro His
            35                  40                  45

Asn Ala Ala Arg Phe Lys Asn Val Leu Asn Arg Ala Ile Glu Ser Gly
50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
            85                  90                  95

Met Ile Pro Phe Phe Lys Ala Val Asn Phe Leu Glu Glu Pro Val Gln
                100                 105                 110

Lys Leu Ile Glu Glu Met Asn Pro Arg Pro Ser Cys Leu Ile Ser Asp
            115                 120                 125

Phe Cys Leu Pro Tyr Thr Ser Lys Ile Ala Lys Lys Phe Asn Ile Pro
130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
            195                 200                 205

Ile Phe Asp Gly Met Val Glu Ala Asn Glu Thr Ser Tyr Gly Val Ile
            210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
```

```
              275                 280                 285
Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
            355                 360                 365

Gly Phe Leu Thr His Cys Gly Trp Asn Ser Thr Leu Glu Gly Ile Thr
        370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Ala Lys Glu Leu Gly Asp
450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495

<210> SEQ ID NO 3
<211> LENGTH: 495
<212> TYPE: PRT
<213> ORGANISM: Arabidopsis thaliana

<400> SEQUENCE: 3

Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
            20                  25                  30

Arg Leu Leu Ala Gln Arg Gly Val Leu Ile Thr Ile Val Thr Thr Pro
        35                  40                  45

His Asn Ala Ala Arg Phe Lys Asn Val Leu Asn Arg Ala Ile Glu Ser
    50                  55                  60

Gly Leu Pro Ile Asn Leu Val Gln Val Lys Phe Pro Tyr Gln Glu Ala
65                  70                  75                  80

Gly Leu Gln Glu Gly Gln Glu Asn Met Asp Leu Leu Thr Thr Met Glu
                85                  90                  95

Gln Ile Thr Ser Phe Phe Lys Ala Val Asn Leu Leu Lys Glu Pro Val
            100                 105                 110

Gln Asn Leu Ile Glu Glu Met Ser Pro Arg Pro Ser Cys Leu Ile Ser
        115                 120                 125

Asp Met Cys Leu Ser Tyr Thr Ser Glu Ile Ala Lys Lys Phe Lys Ile
    130                 135                 140

Pro Lys Ile Leu Phe His Gly Met Gly Cys Phe Cys Leu Leu Cys Val
145                 150                 155                 160
```

-continued

Asn Val Leu Arg Lys Asn Arg Glu Ile Leu Asp Asn Leu Lys Ser Asp
              165                 170                 175
Lys Glu Tyr Phe Ile Val Pro Tyr Phe Pro Asp Arg Val Glu Phe Thr
            180                 185                 190
Arg Pro Gln Val Pro Val Glu Thr Tyr Val Pro Ala Gly Trp Lys Glu
        195                 200                 205
Ile Leu Glu Asp Met Val Glu Ala Asp Lys Thr Ser Tyr Gly Val Ile
    210                 215                 220
Val Asn Ser Phe Gln Glu Leu Glu Pro Ala Tyr Ala Lys Asp Phe Lys
225                 230                 235                 240
Glu Ala Arg Ser Gly Lys Ala Trp Thr Ile Gly Pro Val Ser Leu Cys
                245                 250                 255
Asn Lys Val Gly Val Asp Lys Ala Glu Arg Gly Asn Lys Ser Asp Ile
            260                 265                 270
Asp Gln Asp Glu Cys Leu Glu Trp Leu Asp Ser Lys Glu Pro Gly Ser
        275                 280                 285
Val Leu Tyr Val Cys Leu Gly Ser Ile Cys Asn Leu Pro Leu Ser Gln
    290                 295                 300
Leu Leu Glu Leu Gly Leu Gly Leu Glu Glu Ser Gln Arg Pro Phe Ile
305                 310                 315                 320
Trp Val Ile Arg Gly Trp Glu Lys Tyr Lys Glu Leu Val Glu Trp Phe
                325                 330                 335
Ser Glu Ser Gly Phe Glu Asp Arg Ile Gln Asp Arg Gly Leu Leu Ile
            340                 345                 350
Lys Gly Trp Ser Pro Gln Met Leu Ile Leu Ser His Pro Ser Val Gly
        355                 360                 365
Gly Phe Leu Thr His Cys Gly Trp Asn Ser Thr Leu Glu Gly Ile Thr
    370                 375                 380
Ala Gly Leu Pro Met Leu Thr Trp Pro Leu Phe Ala Asp Gln Phe Cys
385                 390                 395                 400
Asn Glu Lys Leu Val Val Gln Ile Leu Lys Val Gly Val Ser Ala Glu
                405                 410                 415
Val Lys Glu Val Met Lys Trp Gly Glu Glu Lys Ile Gly Val Leu
            420                 425                 430
Val Asp Lys Glu Gly Val Lys Lys Ala Val Glu Glu Leu Met Gly Glu
        435                 440                 445
Ser Asp Asp Ala Lys Glu Arg Arg Arg Ala Lys Glu Leu Gly Glu
    450                 455                 460
Ser Ala His Lys Ala Val Glu Glu Gly Gly Ser Ser His Ser Asn Ile
465                 470                 475                 480
Thr Phe Leu Leu Gln Asp Ile Met Gln Leu Ala Gln Ser Asn Asn
                485                 490                 495

<210> SEQ ID NO 4
<211> LENGTH: 495
<212> TYPE: PRT
<213> ORGANISM: Stevia rebaudiana

<400> SEQUENCE: 4

Met Ser Pro Lys Met Val Ala Pro Thr Asn Leu His Phe Val Leu
1               5                   10                  15
Phe Pro Leu Met Ala Gln Gly His Leu Val Pro Met Val Asp Ile Ala
            20                  25                  30
Arg Ile Leu Ala Gln Arg Gly Ala Thr Val Thr Ile Ile Thr Thr Pro
        35                  40                  45

-continued

```
Tyr His Ala Asn Arg Val Arg Pro Val Ile Ser Arg Ala Ile Ala Thr
     50                  55                  60
Asn Leu Lys Ile Gln Leu Glu Leu Gln Leu Arg Ser Thr Glu Ala
 65                  70                  75                  80
Gly Leu Pro Glu Gly Cys Glu Ser Phe Asp Gln Leu Pro Ser Phe Glu
                 85                  90                  95
Tyr Trp Lys Asn Ile Ser Thr Ala Ile Asp Leu Leu Gln Gln Pro Ala
             100                 105                 110
Glu Asp Leu Leu Arg Glu Leu Ser Pro Pro Asp Cys Ile Ile Ser
             115                 120                 125
Asp Phe Leu Phe Pro Trp Thr Thr Asp Val Ala Arg Arg Leu Asn Ile
 130                 135                 140
Pro Arg Leu Val Phe Asn Gly Pro Gly Cys Phe Tyr Leu Leu Cys Ile
 145                 150                 155                 160
His Val Ala Ile Thr Ser Asn Ile Leu Gly Glu Asn Glu Pro Val Ser
                 165                 170                 175
Ser Asn Thr Glu Arg Val Val Leu Pro Gly Leu Pro Asp Arg Ile Glu
             180                 185                 190
Val Thr Lys Leu Gln Ile Val Gly Ser Ser Arg Pro Ala Asn Val Asp
             195                 200                 205
Glu Met Gly Ser Trp Leu Arg Ala Val Glu Ala Glu Lys Ala Ser Phe
     210                 215                 220
Gly Ile Val Val Asn Thr Phe Glu Glu Leu Glu Pro Glu Tyr Val Glu
 225                 230                 235                 240
Glu Tyr Lys Thr Val Lys Asp Lys Lys Met Trp Cys Ile Gly Pro Val
                 245                 250                 255
Ser Leu Cys Asn Lys Thr Gly Pro Asp Leu Ala Glu Arg Gly Asn Lys
             260                 265                 270
Ala Ala Ile Thr Glu His Asn Cys Leu Lys Trp Leu Asp Glu Arg Lys
             275                 280                 285
Leu Gly Ser Val Leu Tyr Val Cys Leu Gly Ser Leu Ala Arg Ile Ser
 290                 295                 300
Ala Ala Gln Ala Ile Glu Leu Gly Leu Gly Leu Glu Ser Ile Asn Arg
 305                 310                 315                 320
Pro Phe Ile Trp Cys Val Arg Asn Glu Thr Asp Glu Leu Lys Thr Trp
                 325                 330                 335
Phe Leu Asp Gly Phe Glu Glu Arg Val Arg Asp Arg Gly Leu Ile Val
             340                 345                 350
His Gly Trp Ala Pro Gln Val Leu Ile Leu Ser His Pro Thr Ile Gly
             355                 360                 365
Gly Phe Leu Thr His Cys Gly Trp Asn Ser Thr Ile Glu Ser Ile Thr
 370                 375                 380
Ala Gly Val Pro Met Ile Thr Trp Pro Phe Phe Ala Asp Gln Phe Leu
 385                 390                 395                 400
Asn Glu Ala Phe Ile Val Glu Val Leu Lys Ile Gly Val Arg Ile Gly
                 405                 410                 415
Val Glu Arg Ala Cys Leu Phe Gly Glu Glu Asp Lys Val Gly Val Leu
             420                 425                 430
Val Lys Lys Glu Asp Val Lys Lys Ala Val Glu Cys Leu Met Asp Glu
             435                 440                 445
Asp Glu Asp Gly Asp Gln Arg Arg Lys Arg Val Ile Glu Leu Ala Lys
 450                 455                 460
```

Met Ala Lys Ile Ala Met Glu Gly Gly Ser Ser Tyr Glu Asn Val
465                 470                 475                 480

Ser Ser Leu Ile Arg Asp Val Thr Glu Thr Val Arg Ala Pro His
            485                 490                 495

<210> SEQ ID NO 5
<211> LENGTH: 481
<212> TYPE: PRT
<213> ORGANISM: Stevia rebaudiana

<400> SEQUENCE: 5

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Ser Gly Pro His Cys Leu Asp Gly
50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

```
Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370             375                 380

Glu Ser Leu Ser Ala Gly Val Pro Met Ile Cys Trp Pro Tyr Ser Trp
385             390                 395                 400

Asp Gln Leu Thr Asn Cys Arg Tyr Ile Cys Lys Glu Trp Glu Val Gly
            405                 410                 415

Leu Glu Met Gly Thr Lys Val Lys Arg Asp Glu Val Lys Arg Leu Val
            420             425                 430

Gln Glu Leu Met Gly Glu Gly Gly His Lys Met Arg Asn Lys Ala Lys
        435             440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn
```

METHODS AND MATERIALS FOR ENZYMATIC SYNTHESIS OF MOGROSIDE COMPOUNDS

CROSS-REFERENCE TO RELATED APPLICATIONS

This application is a U.S. national phase of International Application No. PCT/IB2012/002857 filed Nov. 19, 2012, which claims the benefit of U.S. Provisional Application No. 61/563,303 filed Nov. 23, 2011. The entire disclosure contents of these applications are herewith incorporated by reference into the present application.

TECHNICAL FIELD

This invention relates to methods and materials for enzymatic synthesis of mogroside compounds, and more particularly to glycosylating mogrol using Uridine-5'-diphospho (UDP) dependent glucosyltransferases (UGTs) to produce various mogroside compounds.

BACKGROUND

Mogrosides are a family of triterpene glycosides isolated from fruits of *Siraitia grosvenorii* (Swingle), also known as *Momordica grosvenori* (Swingle). Extracts of the fruits are commercially used as natural sweeteners. Four major compounds, Mogroside V, Mogroside IV, Siamenoside I, and 11-Oxomogroside V, have been identified from the fruits of *Siraitia grosvenorii* (Swingle) that are responsible for the sweetness of the fruits. See FIG. 1. Mogroside V is the most abundant of these four compounds at approximately 0.57% (w/w) of the dry fruit, followed by Mogroside IV and Siamenoside I, each of which contain four glucose moieties. 11-Oxomogroside V has a ketone group instead of a hydroxyl at C-11. See, e.g., Takemoto, et al., *Yakugaku Zasshi*, 103, 1151-1154; 1155-1166; 1167-1173, (1983); Kasai, et al., *Agric. Biol. Chem.* 53, 3347-3349 (1989); Matsumoto, *Chem. Pharm. Bull.* 38, 2030-2032 (1990); and Prakash, et al., *J. Carbohydrate Chem.* 30, 16-26 (2011).

All mogrosides share the same triterpene core, named mogrol. The aglycone mogrol is glycosylated with different numbers of glucose moieties to form various mogroside compounds. Mogroside is thought to be synthesized in the following manner: synthesis of cucurbitadienol from the common triterpene precursor squalene; P450 oxidations of cucurbitadienol to produce the aglycone mogrol; and glycosylation of mogrol to add the five glucoses one after another to produce mogroside V. See, Tang, et al., *BMC Genomics*, 12, 343 (2011). Both intermediates cucurbitadienol and mogrol exist in the fruit as they have been isolated as minor products. See Ukiya, et al., *J. Agric. Food Chem.* 50, 6710-6715 (2002). Glycoside intermediates exist in both 11-hydroxy and 11-oxo series, and gradually change from mogroside I to mogroside V as fruits ripen, which indicates that the triterpene core is fully oxidized by P450 enzymes before the subsequent glycosylations. However, the enzymes responsible for producing mogrosides have not been identified.

SUMMARY

In one aspect, this document features a method of producing a mogroside compound. The method includes incubating mogrol with a Uridine-5'-diphospho (UDP) dependent glucosyltransferase (UGT) to produce a mogroside compound (e.g., mogroside Ia, mogroside Ib, or a mogroside compound glycosylated at C25-OH). The UGT can be selected from the group consisting of 73C3, 73C6, 85C2, 73C5, and 73E1. The UGTs can be recombinantly produced or can be in a cell lysate of a recombinant host.

This document also features a method of producing a mogroside compound. The method includes contacting mogrol with a cell lysate prepared from a recombinant host expressing a UGT to produce a mogroside compound (e.g., mogroside Ia, mogroside Ib, or a mogroside compound glycosylated at C25-OH). The UGT can be selected from the group consisting of 73C3, 73C6, 85C2, 73C5, and 73E1.

Unless otherwise defined, all technical and scientific terms used herein have the same meaning as commonly understood by one of ordinary skill in the art to which the invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the invention will be apparent from the following detailed description. Applicants reserve the right to alternatively claim any disclosed invention using the transitional phrase "comprising," "consisting essentially of," or "consisting of," according to standard practice in patent law.

DESCRIPTION OF DRAWINGS

FIG. 3 contains the amino acid sequences of the followings UGTs: UGT73C3, UGT73C5, UGT73C6, UGT73E1, and UGT85C2 (SEQ ID NOs: 1-5, respectively).

DETAILED DESCRIPTION

Figure 1:
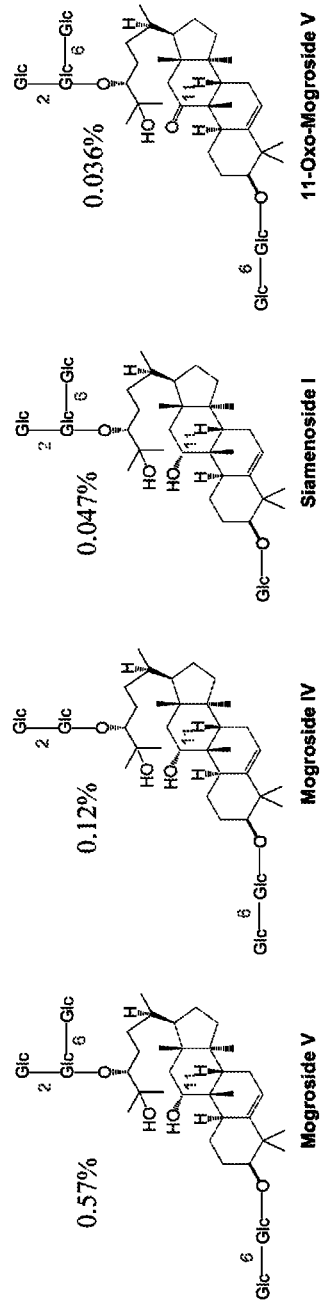
FIG. 1 contains the chemical structure of Mogroside V, Mogroside IV, Siamenoside I, and 11-Oxomogroside V.
Figure 2:
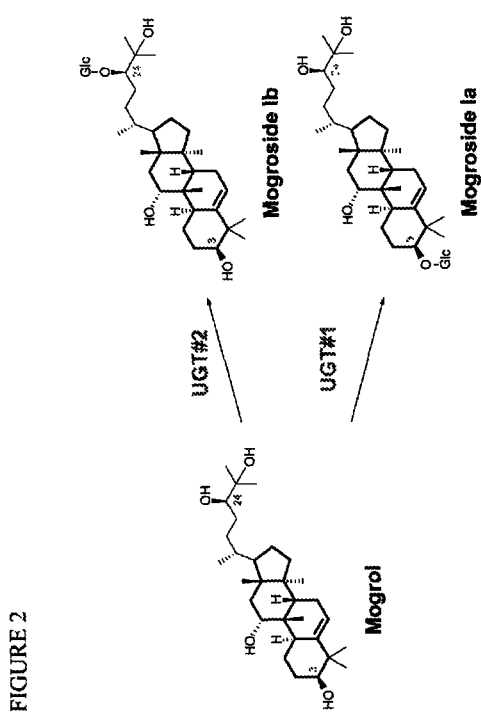
FIG. 2 is a depiction of the biosynthesis of mogroside Ia and mogroside Ib from mogrol using UGTs.

This document provides methods and materials for glycosylating mogrol using one or more Uridine-5'-diphospho (UDP) dependent glucosyltransferases (UGTs). As indicated below, at least five UGTs have been identified that glycosylate the aglycone mogrol. See FIG. 2. Each of the UGTs identified herein are in glycosyltransferase family I. UGTs 73C3, 73C6, 85C2 and 73E1 glycosylate at the C24-OH position (UGT#2 in FIG. 2), while UGT73C5 glycosylates at both the C3-OH (UGT#1 in FIG. 2) and C24-OH position (UGT#2). UGTs 73C3, 73C5, and 73C6 are from *Arabidopsis thaliana*. UGT 73E1 and 85C2 are from *Stevia rebaudiana*. The amino acid sequences of UGTs 73C3, 73C5, 73C6, 73E1, and 85C2 (SEQ ID NOs:1-5) are set forth in FIG. 3.

UGT polypeptides described herein can be produced using any suitable method. For example, UGT polypeptides can be produced by chemical synthesis. Alternatively, a UGT polypeptide described herein can be produced by standard recombinant technology using heterologous expression vectors encoding that UGT polypeptide. Expression vectors can be introduced into host cells (e.g., by transformation or transfection) for expression of the encoded polypeptide, which then can be purified. Expression systems that can be used for small or large scale production of UGT polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules described herein. Useful expression systems also include insect cell systems infected with recombinant virus expression vectors (e.g., baculovirus) containing the nucleic acid molecules described herein, and plant cell systems infected with recombinant virus expression vectors (e.g., tobacco mosaic virus) or transformed with recombinant plasmid expression vectors (e.g., Ti plasmid) containing the nucleic acid molecules described herein. UGT polypeptides also can be produced using mammalian expression system harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids described herein. UGT polypeptides can have an N-terminal or C-terminal tag as discussed below.

This document also provides isolated nucleic acids encoding the UGT polypeptides. An "isolated nucleic acid" refers to a nucleic acid that is separated from other nucleic acid molecules that are present in a genome, including nucleic acids that normally flank one or both sides of the nucleic acid in a genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

In some embodiments, a nucleic acid sequence encoding a UGT polypeptide can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the UGT polypeptide such that the encoded tag is located at either the carboxyl or amino terminus of the UGT polypeptide. Non-limiting examples of encoded tags include green fluorescent protein (GFP), glutathione S transferase (GST), HIS tag, and Flag™ tag (Kodak, New Haven, Conn.). Other examples of tags include a chloroplast transit peptide, a mitochondrial transit peptide, an amyloplast peptide, signal peptide, or a secretion tag.

Functional Homologs

Functional homologs of the polypeptides described above are also suitable for use in the methods and recombinant hosts described herein. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional UGT polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of UGT polypeptides. Sequence analysis can involve BLAST, Reciprocal BLAST, or PSI-BLAST analysis of nonredundant databases using an UGT amino acid sequence as the reference sequence. Amino acid sequence is, in some instances, deduced from the nucleotide sequence. Those polypeptides in the database that have greater than 40% sequence identity are candidates for further evaluation for suitability as a UGT polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in UGT polypeptides, e.g., conserved functional domains.

Conserved regions can be identified by locating a region within the primary amino acid sequence of a polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity. Sequence identity can be determined as set forth above.

Methods of Producing Mogroside Compounds

Mogroside compounds can be produced by incubating a mogrol substrate with one or more of the UGT polypeptides described herein, resulting in the production of a mogroside product. In some embodiments, the reaction mixture contains a plurality of UGT polypeptides such that a plurality of glycosylations occur in the reaction vessel. In other embodiments, the reaction mixture contains a single UGT polypeptide and one or more glycosylations catalyzed by that polypeptide take place. For example, a first reaction vessel can comprise a substrate and one or more UGT polypeptides for producing an intermediate, which can be introduced into a second reaction vessel containing one or more other UGT polypeptides to produce a subsequent intermediate or a mogroside product. The product produced in the second reaction vessel then can be recovered.

Each of the UGT polypeptides can be a purified polypeptide, e.g., can be added to a reaction mixture as a solution containing 80%, 90%, 95%, or greater than 99% by weight of the desired UGT. Alternatively, the UGT polypeptide(s) can be present in a cell lysate prepared from a recombinant host expressing the UGT(s), and can be added to a reaction mixture as a cell lysate for incubation with the mogrol substrate.

Levels of products, substrates and intermediates can be determined by extracting samples from the reaction vessel for analysis according to published methods. Mogroside compounds can be recovered from the reaction vessel using various techniques known in the art.

The invention will be further described in the following examples, which do not limit the scope of the invention described in the claims.

EXAMPLES

Example 1-Purification of Mogroside V

Mogroside V was purified from commercially available monk fruit extracts (PureLo®, Swanson) as follows. Three bottles of PureLo® (240 grams) were dissolved in water (900 mL), then loaded on a column of HP-20 resin (400 gram resin). The column was washed with water (2.5 liters); then further washed with 20% methanol-water. The product was eluted with methanol. After evaporation of solvents and drying under high vacuum, mogroside V (2.5 grams, ~80% purity, 11-oxomogroside V was the major impurity) was obtained.

Example 2—Enzymatic Synthesis of Mogrol from Mogroside V

Figure 4:
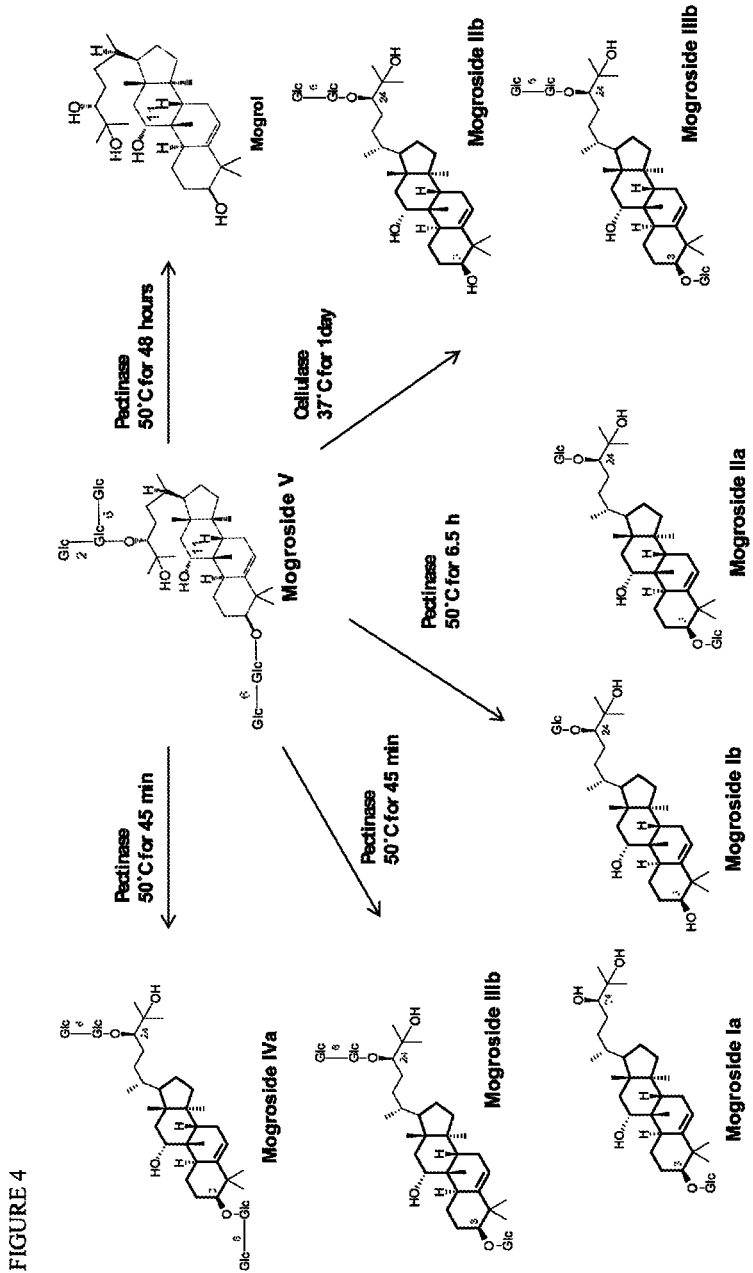
FIG. 4 is a schematic of the products obtained from mogroside V after incubation with a pectinase and/or a cellulase.

Mogroside V (300 mg) was dissolved in 0.1 M sodium acetate buffer (pH 4.5, 100 mL), and crude pectinase from *Aspergillus niger* (25 mL, Sigma P2736) was added. The mixture was stirred at 50° C. for 48 hours. The reaction mixture was extracted with ethyl acetate (2×100 ml). The organic extract was dried under vacuum then purified with preparative HPLC. Pure mogrol (40 mg) was obtained and its structure confirmed by NMR and mass spectroscopy. See FIG. 4.

Example 3—Enzymatic Synthesis of Mogrol 3-O-Glucoside (Mogroside Ia) and Mogrol 24-O-Glucoside (Mogroside Ib) from Mogroside V Mogroside V (300 mg) was dissolved in 0.1 M sodium acetate buffer (pH 4.5, 100 ml), and crude pectinase from *Aspergillus niger* (25 ml, Sigma P2736) was added. The mixture was stirred at 50° C. for 6.5 hours. The reaction mixture was extracted with ethyl acetate (2×100 ml). The organic extract was dried under vacuum then purified with preparative HPLC. Pure mogroside Ia (11.0 mg) and mogroside Ib (8.0 mg) were obtained. Their structures were confirmed by NMR and mass spectroscopy. See FIG. 4.

Example 4—In Vitro UGT Screening and Reactions

In vitro reactions of mogrol with a panel of 230 UGT enzymes were performed and the products were analyzed with LC-MS. The in vitro UGT reaction mixtures included 4× Tris buffer, mogrol (250 μM), UDP-glucose (750 μM) and 1% alkaline phosphatase. Five μl of each partially purified UGT enzyme or crude enzyme extract was added to the reaction, and the reaction volume brought to 50 μl with water. The reactions were incubated overnight at 30° C. and performed in sterilized 96 well plates. After the incubation, 25 μL of DMSO were added into each reaction and the reaction plates were centrifuged for 5 min. Forty μL samples were taken from each well and filtered, and were used for LC-MS analysis.

UGTs 73C3, 73C6 and 85C2 were found to convert all the mogrol substrate to mogroside Ib. UGT 73C5 makes both mogroside Ia and Ib. In the reaction with UGT 73E1, although the reaction was not complete, mogroside Ib was found as the major product, together with a new glycosylated mogrol (neither mogroside Ia nor Ib; exact mass shown as a mogroside I, presumably caused by a glycosylation event on C25-OH).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method for producing a mogroside compound, comprising:
   (a) adding one or more isolated recombinant polypeptides capable of catalyzing glycosylation of mogrol to produce a mogroside compound and having at least 90% sequence identity to the amino acid sequence set forth in SEQ ID NOs:1-5 and a plant-derived or synthetic mogrol to a reaction mixture; and synthesizing the mogroside compound thereby; and
   (b) recovering the mogroside compound produced in step (a) from the reaction mixture.

2. An in vitro method for producing a mogroside compound, comprising:
   (a) adding a cell lysate prepared from a recombinant host expressing one or more recombinant polypeptides capable of catalyzing glycosylation of mogrol to produce a mogroside compound and having at least 90% sequence identity to the amino acid sequence set forth in SEQ ID NOs:1-5 and a plant-derived or synthetic mogrol to a reaction mixture; and synthesizing the mogroside compound thereby; and
   (b) recovering the mogroside compound produced in step (a) from the reaction mixture.

3. An in vitro method for producing a mogroside compound, comprising:
   (a) (i) adding one or more isolated recombinant polypeptides capable of catalyzing glycosylation of mogrol to produce a mogroside compound and having at least 90% sequence identity to the amino acid sequence set forth in SEQ ID NOs:1-5 and a plant-derived or synthetic mogrol to a reaction mixture; and producing the mogroside compound thereby;
      wherein the one or more isolated recombinant polypeptides is produced in a recombinant host or by chemical synthesis; and
      (ii) recovering the mogroside compound produced in step (a)(i) from the reaction mixture;
   (b) (i) adding a cell lysate prepared from a recombinant host expressing one or more recombinant polypeptides capable of catalyzing glycosylation of mogrol to produce a mogroside compound and having at least 90% sequence identity to the amino acid sequence set forth in SEQ ID NOs:1-5 and a plant-derived or synthetic mogrol to a reaction mixture; and synthesizing the mogroside compound thereby; and
      (ii) recovering the mogroside compound produced in step (b)(i) from the reaction mixture;
   (c) (i) contacting and glycosylating mogrol in a first reaction vessel with one or more isolated recombinant polypeptides capable of catalyzing glycosylation of mogrol to produce a mogroside compound and having at least 90% sequence identity to the amino acid sequence set forth in SEQ ID NOs:1-5, thereby producing an intermediate compound;
      (ii) contacting and glycosylating the intermediate compound in a second reaction vessel with the one or more isolated recombinant polypeptides capable of catalyzing glycosylation of mogrol to produce a mogroside compound and having at least 90% sequence identity to the amino acid sequence set forth in SEQ ID NOs:1-5;
      wherein the one or more isolated polypeptides is produced in a recombinant host or by chemical synthesis; and
      (iii) recovering the mogroside compound produced in step (c)(ii); or
   (d) (i) contacting and glycosylating mogrol in a first reaction vessel with a cell lysate prepared from a recombinant host expressing one or more recombinant polypeptides capable of catalyzing glycosylation of mogrol to produce a mogroside compound and having at least 90% sequence identity to the amino acid sequence set forth in SEQ ID NOs:1-5, thereby producing an intermediate compound;
      (ii) contacting and glycosylating the intermediate compound in a second reaction vessel with one or more isolated recombinant polypeptides capable of catalyzing glycosylation of mogrol to produce a mogroside compound and having at least 90% sequence identity to the amino acid sequence set forth in SEQ ID NOs:1-5; and (iii) recovering the mogroside compound produced in step (d)(ii).

4. The method of any one of claim 1, 2 or 3, wherein:
(a) the glycosylation is effected by the activity of the polypeptide having at least 90% sequence identity to the amino acid sequence set forth in SEQ ID NO:2 and the mogroside compound is mogroside Ia;
(b) the glycosylation is effected by the activity of one or more of the polypeptides having at least 90% sequence identity to the amino acid sequence set forth in SEQ ID NOs:1-5 and the mogroside compound is mogroside Ib; or
(c) the glycosylation is effected by the activity of the polypeptide having at least 90% sequence identity to the amino acid sequence set forth in SEQ ID NO:4 and the mogroside compound is a mogroside compound glycosylated at C25-OH.

5. The method of claim 1, wherein the one or more isolated recombinant polypeptide is produced in a recombinant host.

6. The method of any one of claim 1, 2 or 3, wherein the polypeptide capable of catalyzing glycosylation of mogrol to produce a mogroside compound comprises a tag sequence located at either a carboxyl or an amino terminus of the polypeptide.

7. The method of claim 6, wherein the tag sequence comprises a green fluorescent protein (GFP), a glutathione S transferase (GST), a HIS tag, a Flag tag, a chloroplast transit peptide, a mitochondrial transit peptide, an amyloplast peptide, a signal peptide, or a secretion tag.

8. The method of any one of claim 2, 3 or 5, wherein the recombinant host is a microorganism transformed with recombinant bacteriophage DNA, plasmid DNA, or cosmid DNA expression vectors.

9. The method of any one of claim 2, 3 or 5, wherein the recombinant host is an insect cell system infected with recombinant virus expression vectors.

10. The method of any one of claim 2, 3 or 5, wherein the recombinant host is a plant cell system infected with recombinant virus expression vectors or transformed with recombinant virus expression vectors.

11. The method of any one of claim 2, 3 or 5, wherein the recombinant host is a mammalian expression system harboring recombinant expression constructs comprising promoters derived from the genome of mammalian cells or from mammalian viruses.

12. An in vitro method for transferring a sugar moiety to a C24' position, C3' position, both C24' and C3' positions, or C25' position of mogrol, comprising:

contacting the mogrol with one or more isolated recombinant polypeptides having at least 90% sequence identity to the amino acid sequence set forth in SEQ ID NOs:1-5, capable of C24' glycosylation, C3' glycosylation, both C24' glycosylation and C3' glycosylation, or C25' glycosylation of mogrol, and a UDP-sugar under suitable reaction conditions for the transfer of the sugar moiety to the mogrol,
wherein a mogroside Ia, mogroside Ib, a mogroside compound glycosylated at C25-OH, an isomer thereof, and/or a mogroside composition thereof is produced upon transfer of the sugar moiety.

13. The method of claim 12, wherein:
(a) the sugar moiety is glucose, the glycosylation is effected by the activity of the polypeptide having at least 90% sequence identity to the amino acid sequence set forth in SEQ ID NO:2, and mogroside Ia is produced upon transfer of the glucose moiety to mogrol;
(b) the sugar moiety is glucose, the glycosylation is effected by the activity of one or more of the polypeptides having at least 90% sequence identity to the amino acid sequence set forth in SEQ ID NOs:1-5, and mogroside Ib is produced upon transfer of the glucose moiety to mogrol; or
(c) the sugar moiety is glucose, the glycosylation is effected by the activity of the polypeptide having at least 90% sequence identity to the amino acid sequence set forth in SEQ ID NO:4, and mogroside I is produced upon transfer of the glucose moiety to mogrol.

14. The method of claim 12, wherein the mogroside compound is mogroside Ia;
wherein the glycosylation is effected by the activity of the polypeptide having at least 90% sequence identity to the amino acid sequence set forth in SEQ ID NO:2.

15. The method of claim 12, wherein the mogroside compound is mogroside Ib;
wherein the glycosylation is effected by the activity of one or more of the polypeptides having at least 90% sequence identity to the amino acid sequence set forth in SEQ ID NOs:1-5.

16. The method of claim 12, wherein the mogroside compound is a mogroside compound glycosylated at C25-OH;
wherein glycosylation is effected by the activity of the polypeptide having at least 90% sequence identity to the amino acid sequence set forth in SEQ ID NO:4.

\* \* \* \* \*